United States Patent [19]

Trecek et al.

[11] 4,258,216

[45] Mar. 24, 1981

[54] VAPOR PHASE OXIDATION PROCESS FOR GLYOXAL

[75] Inventors: James B. Trecek, Wayne; George L. Wiesner, Bound Brook, both of N.J.

[73] Assignee: American Cyanamid Company, Stamford, Conn.

[21] Appl. No.: 27,706

[22] Filed: Apr. 9, 1979

Related U.S. Application Data

[63] Continuation-in-part of Ser. No. 600,560, Jul. 31, 1975, abandoned.

[51] Int. Cl.$^3$ .............................................. C07C 45/38
[52] U.S. Cl. ...................................... 568/473; 568/471
[58] Field of Search ............... 260/603 R, 603 C, 602; 568/471, 473

[56] References Cited

U.S. PATENT DOCUMENTS

| | | | |
|---|---|---|---|
| 2,339,282 | 1/1944 | McNamee et al. | 260/603 C |
| 2,339,346 | 1/1944 | McNamee et al. | 260/603 C |
| 2,339,348 | 1/1944 | McNamee et al. | 260/603 C |
| 3,948,997 | 4/1976 | Howe et al. | 260/603 C |

FOREIGN PATENT DOCUMENTS 1272592  5/1972  United Kingdom ..................... 260/603

*Primary Examiner*—Werren B. Lone
*Attorney, Agent, or Firm*—Bruce F. Jacobs

[57] ABSTRACT

The process for preparing glyoxal from ethylene glycol wherein a gaseous mixture of ethylene glycol, oxygen, and inert diluent gas is reacted in the presence of a catalyst containing as essential ingredients phosphorous with copper, with silver, or with both copper and silver, to form glyoxal, is improved by incorporating in said gaseous mixture a vapor of a bromine compound.

10 Claims, No Drawings

VAPOR PHASE OXIDATION PROCESS FOR GLYOXAL

This application is a continuation-in-part of U.S. Pat. No. 600,560, filed July 31, 1975, abandoned.

This application relates to an improved process for preparing glyoxal from ethylene glycol. More particularly, it relates to improving the yield of a high conversion, vapor phase oxidation process wherein ethylene glycol is oxidized to glyoxal in the presence of a catalyst containing phosphorous with copper, with silver, or with both copper and silver as essential ingredients.

British Pat. No. 1,272,592, published May 3, 1972, discloses a process for vapor phase oxidation of ethylene glycol to form glyoxal in the presence of certain catalysts, which catalysts contain copper and/or silver along with phosphorous as a promoter. As can be seen from the experimental data in said British Patent, there is a very high conversion of ethylene glycol with a fair yield of glyoxal and substantial production of undesired by-products. It is an object of the present invention to modify this process to obtain improved yields of glyoxal while maintaining the conversion of ethylene glycol at the very high level.

Long prior to said British Patent, it was known to oxidize ethylene glycol to form glyoxal by a vapor phase oxidation process in the presence of a catalyst containing copper and that, as described in U.S. Pat. Nos. 2,339,282 and 2,339,346 the yield of glyoxal could be improved by addition of a small amount (e.g., 0.02% or 200 ppm of gas mixture) of ethylene dichloride to the gas mixture being oxidized. When such approach was tried using the catalyst of the above-cited British Patent, the improvement in yield was inadequate. In accordance with the present invention, it has been discovered that a substantial improvement in the yield of glyoxal while maintaining the very high conversion of ethylene glycol could be achieved in the vapor phase oxidation process using a catalyst containing, as essential ingredients, phosphorous with copper, with silver, or with both copper and silver can be achieved by incorporating in the gaseous mixture of ethylene glycol, oxygen, and inert diluent gas an effective amount of a vapor of a bromine compound.

Illustrative of the various bromine compounds whose vapors can be used in the practice of the present invention are the bromoalkanes, such as methyl bromide, methylene bromide, bromoform, tetrabromomethane, ethyl bromide, ethylene dibromide, tribromoethane, propyl bromide, dibromopropane, tribromopropane, butyl bromide, dibromobutane, amyl bromide, dibromopentane, hexyl bromide, and octyl bromide; phenyl bromide, benzyl bromide, dibromobenzene, hydrogen bromide, and phosphorous tribromide.

The concentration of the vapor of the bromine compound in gaseous mixture of ethylene glycol, oxygen, and inert diluent gas should be high enough to be effective for significantly increasing the yield of glyoxal produced as compared with control runs omitting the bromine compound. In general, such minimum concentration is about 0.5 parts bromine compound per million parts of gaseous mixture. Excessive concentrations of vapor of the bromine compound are to be avoided as such excesses increase glycol aldehyde formation and reduce the conversion of ethylene glycol to below about 90%. While the maximum concentration useable is, to some extent, a function of specific operating conditions in the reactor and of the specific bromine compound used, in general such maximum concentration is about 32 parts bromine compound per million parts of gaseous mixture. The optimum concentration will normally be selected for actual use in practicing this invention and such optimum concentration will generally be within the range of 0.5 to 30, most preferably, 1 to 20 parts bromine per million parts gaseous mixture.

The catalyst used in this process, its composition, its method of preparation, and its method of use are all described in British Pat. No. 1,272,592. While all the novel catalysts there disclosed are useful for the present invention, as a practical matter, selection of those catalysts and reactant ratios disclosed in said British Patent to be best are to be preferred for use in the present invention. The catalyst may be in any of the physical forms described in said British Patent, such as alloy in the form of turnings, gauze, etc., intimate particulate mixture of the essential constituents of the catalyst, or supported on inorganic support material, etc. A preferred form is as a mixture of active catalyst with inert ceramic diluent, such as pellets, saddles, or other shapes. Preferably, such mixture can be an approximately equivolume mixture of active catalyst and inert ceramic diluent.

The following examples will serve to illustrate a preferred embodiment and some alternate embodiments of the present invention, and comparison runs wherein the bromine compound is omitted. In each example, the oxygen was supplied as air and the inert diluent gas comprised the remainder of the molecular species in the air plus recycle gas not condensed in the scrubber.

EXAMPLES

In each of the following examples, a hot gaseous mixture of ethylene glycol, oxygen, and inert diluent gas of the indicated molar proportions with or without the indicated concentration of the specified bromine compound is fed at the indicated feed rate to a heated reactor containing a four-foot bed of an equivolume blend of $\frac{1}{4}''$ diameter $\times \frac{3}{8}''$ length cylindrical ceramic pellets and an oxidation catalyst consisting of 88.1% copper, 9.6% silver, and 2.3% phosphorous. In the following examples, the inlet gas temperature, maximum temperature in reactor, and outlet temperatures are given for each run along with the contact time of the gases with the catalyst and the yields and conversions achieved. In each example, the process was operated for several hours to achieve equilibrium operations prior to obtaining the samples whose results are reported below. After exiting from the reactor, the gases were passed through a scrubber and the condensables were recovered as an aqueous solution containing glyoxal.

EXAMPLE 1

Gas mixture composition was 1 mole ethylene glycol to 1.20 moles oxygen to 53 moles inert gas. No bromine compound was added. Feed rate to the reactor was 1.44 pounds ethylene glycol per hour. Inlet gas temperature was 292° C., maximum temperature in reactor was 458° C.; outlet temperature was 427° C.; and contact time was about 1 second. The conversion was 98.8% of the ethylene glycol and the yield was 62.0% glyoxal.

EXAMPLE 2

Gas mixture composition was 1 mole ethylene glycol to 1.20 moles oxygen to 55 moles inert gas. No bromine compound was added. Feed rate to the reactor was 1.45 pounds ethylene glycol per hour. Inlet gas temperature was 318° C.; maximum temperature in reactor was 454° C.; outlet temperature was 426° C., and contact time was about 1 second. The conversion was 97.7% of the ethylene glycol and the yield was 63.4% glyoxal.

EXAMPLE 3

Gas mixture composition was 1 mole ethylene glycol to 1.14 moles oxygen to 56 moles inert gas. No bromine compound was added. Feed rate to the reactor was 1.44 pounds ethylene glycol per hour. Inlet gas temperature was 251° C.; maximum temperature in reactor was 455° C.; outlet temperature was 455° C.; and contact time was 1.25 seconds. The conversion was 96.0% of the ethylene glycol and the yield was 63.9% glyoxal.

EXAMPLE 4

Gas mixture composition was 1 mole ethylene glycol to 1.30 moles oxygen to 57 moles inert gas. Sufficient ethylene dibromide was dissolved in the ethylene glycol to provide 2 parts ethylene dibromide (equivalent to 1.7 parts bromine) per million parts gas mixture. Feed rate to the reactor was 1.45 pounds ethylene glycol per hour. Inlet gas temperature was 292° C.; maximum temperature in reactor was 450° C.; outlet temperature was 450° C.; and contact time was about 1 second. The conversion was 98.1% of the ethylene glycol and the yield was 74.5% glyoxal. This example illustrates the substantial improvement in yield of glyoxal achieved at high conversion of ethylene glycol when the gaseous mixture contained as little as 1.7 parts bromine as ethylene dibromide per million parts gas mixture.

EXAMPLE 5

Gas mixture composition was 1 mole ethylene glycol to 1.24 moles oxygen to 54 moles inert gas. Sufficient ethylene dibromide was dissolved in the ethylene glycol to provide 5 parts ethylene dibromide (equivalent to 4.3 parts bromine) per million parts gas mixture. Feed rate to the reactor was 1.43 pounds ethylene glycol per hour. Inlet gas temperature was 308° C.; maximum temperature in reactor was 440° C.; outlet temperature was 440° C.; and contact time was about 1 second. The conversion was 99.3% of the ethylene glycol and the yield was 76.9% glyoxal. This example also illustrates the substantial improvement in yield of glyoxal achieved at high conversion of ethylene glycol when the gaseous mixture contained 4.3 parts bromine as ethylene dibromide per million parts gas mixture.

EXAMPLE 6

Gas mixture composition was 1 mole ethylene glycol to 1.14 moles oxygen to 56 moles inert gas. Sufficient ethylene dibromide was dissolved in the ethylene glycol to provide 0.75 parts ethylene dibromide (equivalent to 0.64 parts bromine) per million parts gas mixture. Feed rate to the reactor was 1.44 pounds ethylene glycol per hour. Inlet gas temperature was 263° C.; maximum temperature in reactor was 473° C.; outlet temperature was 443° C.; and contact time was about 1 second. The conversion was 97.5% of the ethylene glycol and the yield was 76.7% glyoxal. This example illustrates improved yield of glyoxal at high conversion of ethylene glycol when the gaseous mixture contained as little as 0.64 parts bromine as ethylene dibromide per million parts gas mixture. Thus, while this low a concentration of bromine compound is capable of producing improved yield, it would not be preferred when compared to the concentrations of Examples 4 and 5, supra.

EXAMPLE 7

Gas mixture composition was 1 mole ethylene glycol to 1.40 moles oxygen to 55 moles inert gas. Sufficient ethylene dibromide was dissolved in the ethylene glycol to provide 40 parts ethylene dibromide (equivalent to 34 parts bromine) per million parts gas mixture. Feed rate to the reactor was 1.44 pounds ethylene glycol per hour. Inlet gas temperature was 276° C.; maximum gas temperature in reactor was 468° C.; outlet temperature was 468° C.; and contact time was about 1 second. The conversion was 87.0% of the ethylene glycol and the yield was 65.0% glyoxal. This example illustrates the undesirable loss of conversion efficiency when too high a concentration of bromine compound is used.

EXAMPLE 8

Gas mixture composition was 1 mole ethylene glycol to 1.35 moles oxygen to 53 moles inert gas. Sufficient bromobenzene was added to provide 15 parts bromobenzene (equivalent to 7.6 parts bromine) per million parts gas mixture. Feed rate to the reactor was 1.42 pounds ethylene glycol per hour. Inlet gas temperature was 289° C.; maximum temperature in the reactor was 458° C.; outlet temperature was 458° C.; and contact time was about 1 second. The conversion was 97% of the ethylene glycol and the yield was 72% glyoxal. This example illustrates the usefulness of an aromatic bromine compound, bromobenzene, for substantially improving the yield of glyoxal while maintaining high conversion of ethylene glycol.

EXAMPLE 9

Gas mixture composition was 1 mole ethylene glycol to 1.24 moles oxygen to 59 miles inert gas. Sufficient bromoform was added to provide 20 parts bromoform (equivalent to 18.4 parts bromine) per million parts gas mixture. Feed rate to the reactor was 1.42 pounds ethylene glycol per hour. Inlet gas temperature was 294° C.; maximum temperature in the reactor was 450° C.; outlet temperature was 450° C.; and contact time was about 1 second. The conversion was 99.4% of the ethylene glycol and the yield was 79.8% glyoxal. This example illustrates the usefulness of another aliphatic bromine compound, bromoform, for substantially improving the yield of glyoxal while maintaining high conversion of ethylende glycol.

EXAMPLE 10

Gas mixture composition was 1 mole ethylene glycol to 1.28 moles oxygen to 57 moles inert gas. Sufficient 48% aqueous hydrogen bromide was added to provide 4.8 parts HBr (equivalent to 4.7 parts bromine) per million parts gas mixture. Feed rate to the reactor was 1.44 pounds ethylene glycol per hour. Inlet gas temperature was 291° C.; maximum temperature in the reactor was 450° C.; outlet temperature was 450° C.; and contact time was about 1 second. The conversion was 99.8% of the ethylene glycol and the yield was 79.6% glyoxal. This example illustrates the usefulness of an inorganic bromine compound, hydrogen bromide, for substantially improving the yield of glyoxal while maintaining high conversion of ethylene glycol.

EXAMPLE 11

Gas mixture composition was 1 mole ethylene glycol to 1.30 moles oxygen to 55 moles inert gas. Sufficient phosphorous tribromide was added to provide 5 parts phosphorous tribromide (equivalent to 4.4 parts bromine) per million parts gas mixture. Feed rate to the reactor was 1.44 pounds ethylene glycol per hour. Inlet gas temperature was 288° C.; maximum temperature in the reactor was 450° C.; outlet temperature was 450° C.; and contact time was about 1 second. The conversion was 99.9% of the ethylene glycol and the yield was 80.5% glyoxal. This example illustrates the usefulness of another inorganic bromine compound, phosphorous tribromide, for substantially improving the yield of glyoxal while maintaining high conversion of ethylene glycol.

What is claimed is:

1. In the process of preparing glyoxal from ethylene glycol wherein a gaseous mixture of ethylene glycol, oxygen, and inert diluent gas is reacted at a temperature of between 180° C. and 600° C. in the presence of a catalyst containing as essential ingredients phosphorous with copper, with silver, or with both copper and silver, to form glyoxal, the improvement comprising incorporating in said gaseous mixture about 0.5 to 32 ppm. of a vapor of a bromine compound selected from the group consisting of bromoalkanes, arylbromides, and phosphorous tribromide.

2. The process of claim 1 wherein said bromine compound is a bromoalkane.

3. The process of claim 2 wherein said bromoalkane is alkyl bromide of 1 to 8 carbon atoms, dibromoalkane of 1 to 5 carbon atoms, tribromoalkane of 1–3 carbon atoms, or carbon tetrabromide.

4. The process of claim 3 wherein said bromoalkane contains 1 to 3 carbon atoms and 1 to 3 bromine atoms.

5. The process of claim 4 wherein said bromoalkane is ethylene dibromide.

6. The process of claim 1 wherein said bromine compound is phenyl bromide, benzyl bromide, dibromobenzene, or phosphorous tribromide.

7. The process of claim 1 wherein said bromine compound is utilized in an amount between 1 and 15 parts bromine compound per million parts of said gaseous mixture.

8. The process of claim 1 wherein said catalyst is in the form of an equivolume mixture of active catalyst and inert ceramic diluent.

9. The process of claim 1 wherein said bromine compound is bromoform.

10. The process of claim 6 wherein said bromine compound is phosphorous tribromide.

* * * * *